(12) United States Patent
Tsukabayashi et al.

(10) Patent No.: US 9,017,612 B2
(45) Date of Patent: Apr. 28, 2015

(54) GAS SENSOR

(75) Inventors: Shunji Tsukabayashi, Saitama (JP);
Hidetoshi Oishi, Saitama (JP);
Kazuhiro Okajima, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 462 days.

(21) Appl. No.: 13/463,188

(22) Filed: May 3, 2012

(65) Prior Publication Data
US 2012/0288411 A1 Nov. 15, 2012

(30) Foreign Application Priority Data

May 11, 2011 (JP) ................................ 2011-106666

(51) Int. Cl.
*G01N 15/06* (2006.01)
*G01N 27/16* (2006.01)
*G01N 33/00* (2006.01)
*H01M 8/04* (2006.01)

(52) U.S. Cl.
CPC .............. *G01N 27/16* (2013.01); *G01N 33/005* (2013.01); *H01M 8/04089* (2013.01); *Y02E 60/50* (2013.01)

(58) Field of Classification Search
USPC ............................... 422/83, 98, 94, 95, 96, 97
See application file for complete search history.

(56) References Cited

U.S. PATENT DOCUMENTS

| | | | |
|---|---|---|---|
| 4,510,036 A * | 4/1985 | Takeuchi et al. ............... | 204/425 |
| 5,831,146 A | 11/1998 | Newman | |
| 5,886,614 A | 3/1999 | Cheng et al. | |
| 2011/0158854 A1 | 6/2011 | Yamagishi et al. | |
| 2012/0090380 A1 | 4/2012 | Wetzig | |

FOREIGN PATENT DOCUMENTS

| | | |
|---|---|---|
| DE | 198 08 663 A1 | 11/1999 |
| DE | 697 05 021 T2 | 9/2001 |
| DE | 698 08 553 T2 | 2/2003 |
| DE | 10 2004 060 103 A1 | 12/2005 |
| DE | 10 2009 030 180 A1 | 12/2010 |
| DE | 10 2010 053 366 A1 | 6/2011 |
| JP | H07-012771 A | 1/1995 |
| JP | 2003-166963 A | 6/2003 |

(Continued)

OTHER PUBLICATIONS

German Search Report application No. 10 2012 207 966.1 issued Sep. 13, 2012.

(Continued)

*Primary Examiner* — Brian J Sines
(74) *Attorney, Agent, or Firm* — Squire Patton Boggs (US) LLP

(57) ABSTRACT

Provided is a gas sensor that needs no temperature sensor for detecting a temperature of a heater for preventing dew condensation. The gas sensor comprises a hydrogen sensor 1 including: an element housing 13 having a detection chamber 13a to which hydrogen is introduced; a detection element 31 arranged in the detection chamber 13a and detecting hydrogen; a heater 21 for heating the detection chamber 13a by heat generation via passing an electric current through the heater 21, a resistance value of the heater 21 being changed corresponding to a temperature of the detection chamber 13a; and a microcomputer 51 and a heater operation circuit 52 for controlling the heater 21. Herein, the microcomputer 51 controls a temperature of the detection chamber 13a by adjusting the electric current passing through the heater 21 based on the resistance value of the heater 21.

6 Claims, 11 Drawing Sheets

(56) References Cited

FOREIGN PATENT DOCUMENTS

| | | |
|---|---|---|
| JP | 2003-294675 A | 10/2003 |
| JP | 2007-309905 A | 11/2007 |
| JP | 2009-030975 A | 2/2009 |

OTHER PUBLICATIONS

JP Office Action for JP Application No. 2011-10666, dated Mar. 19, 2013.

* cited by examiner

<OUTPUT CORRECTION>

GAS SENSOR

CROSS REFERENCE TO RELATED APPLICATIONS

This application claims the foreign priority benefit under Title 35, United State Code, 119 (a)-(d) of Japanese Patent Application No. 2011-106666, filed on May 11, 2011 in the Japan Patent Office, the disclosure of which is herein incorporated by reference in its entirety.

BACKGROUND OF THE INVENTION

1. Field of the Invention

The present invention relates to a gas sensor.

2. Description of Related Art

Recently, a fuel cell which is expected for a power source for a fuel cell vehicle or the like discharges hydrogen (or gas to be detected) not consumed by power generation from an anode of the fuel cell. The hydrogen is diluted with cathode off-gas (or dilution gas) flowing from a cathode of the fuel cell, and subsequently discharged to the outside of the vehicle (or outside). Then, the concentration of hydrogen in the gas discharged to the outside of the vehicle (or diluted gas) is detected by a hydrogen sensor (or gas sensor).

Accompanying the power generation, the fuel cell also generates moisture (or steam) in the cathode, which makes the cathode off-gas and the diluted gas flowing toward the hydrogen sensor become a high humidity gas. Herein, if the steam contained in the diluted gas condenses to be dew condensation water thereby being attached to a detector element of the hydrogen sensor, detection sensitivity of hydrogen becomes to be lowered.

To address the above mentioned drawback, Japanese Laid-Open Patent Publication No. 2003-294675 proposes a hydrogen sensor comprising a heater (or heating unit). Herein, the hydrogen sensor with a heater prevents the generation of the dew condensation water, and also prevents the dew condensation water from being attached to the detector element. Note the output of the heater is controlled by a temperature sensor arranged at a vicinity of the heater such that the generation and the attachment of the dew condensation water may be prevented based on a temperature of the heater detected by the temperature sensor.

However, as mentioned hereinbefore, if the temperature sensor for detecting the heater temperature is included, the number of the components of the hydrogen sensor increases, resulting in the difficulty and inconvenience for downsizing the hydrogen sensor.

SUMMARY OF THE INVENTION

Accordingly, an object of the present invention is to provide a gas sensor which needs no temperature sensor for detecting a temperature of a heater for preventing dew condensation.

In order to solve the aforementioned drawback, a gas sensor of the present invention comprises: an element housing including a detection chamber in which gas to be detected is introduced; a detection element arranged in the detection chamber and detecting gas to be detected; a heater for heating the detection chamber by generating heat through the passage of an electric current, a resistance value of the heater being changed corresponding to the temperature of the heater; and a control unit for controlling the heater. Herein, the control unit controls the temperature of the detection chamber by controlling the electric current passing through the heater based on the resistance value of the heater.

In the above mentioned construction, the resistance value of the heater is changed corresponding to the temperature of the heater. This allows the temperature of the heater and the temperature of the detection chamber to be estimated based on the resistance value of the heater. Accordingly, the control unit may estimate the temperature of the detection chamber based on the resistance value of the heater, thereby to control the temperature of the detection chamber such that no dew condensation water is generated by controlling the passage of the electric current through the heater.

As mentioned above, a temperature sensor for detecting a temperature of the heater becomes unnecessary, and hereby the number of the components of the gas sensor becomes fewer, allowing the gas sensor to be constructed in more downsizing and lower costs.

Here, preferably the gas sensor further comprises a bridge circuit composed of the heater, an A resistor, a B resistor and a C resistor. Also, preferably the control unit comprises a heater operation circuit for feeding back a potential difference outputted by the bridge circuit, thereby to control the electric current through the heater.

According to the above mentioned construction, the heater operation circuit in the control unit feeds back the potential difference outputted by the bridge circuit so as to control the electric current through the heater, allowing the temperature of the detection chamber to be controlled. This enables a control process of the heater following a control program or the like in the control unit to become unnecessary; the control process being a heater control process shown in FIG. 8, described in an embodiment hereinafter.

Further, in the gas sensor, preferably the control unit controls the temperature of the detection chamber to be kept over a temperature of preventing dew condensation such that the dew condensation in the detection chamber may be prevented.

The above mentioned construction allows the dew condensation in the detection chamber to be prevented because the control unit controls the temperature of the detection chamber to be kept over a temperature of preventing the dew condensation.

Further, in the gas sensor, the detection element is a catalytic combustion element. Preferably, the control unit corrects an output value of the detection element based on the resistance value of the heater.

Here, the detection elements in a catalytic combustion type is constructed so as to burn the detected gas which contacts with the detection element, and thereby to increase a temperature of the detection elements by the resulting combustion heat. Further, the detection element is made of a material (platinum or the like) of which resistance value is changed corresponding to the temperature of the material. Hereby, when the temperature of the detection element increases, the resistance value of the detection element is changed. Thus, the change of the resistance value of the detection element is used to detect a concentration of the detected gas.

However, note a temperature and a resistance value of the detection element are changed corresponding to the temperature of the detection chamber (or environmental temperature) in which the detection element is arranged, even though a concentration of the detected gas is 0 (or combustion heat is 0). Therefore, the concentration of the detected gas needs to be calculated considering the above mentioned characteristics of the detection element.

For that purpose, a technique for detecting a concentration of gas to be detected has been developed and disclosed, comprising the steps of: arranging a temperature compensation element at a vicinity of the detection element, the temperature compensation element being inactive to the gas to be detected but a temperature and a resistance value of the temperature compensation element being changed corresponding to a temperature of the detection chamber; constructing a bridge circuit including the detection element and the temperature compensation element; offsetting the resistance value of the temperature compensation element from the resistance value of the detection element by the bridge circuit; and outputting a voltage value calculated by only the combustion heat of the gas to be detected, the gas being combusted by the detection element.

However, in the above mentioned technique, the temperature compensation element has to be arranged in the vicinity of the detection element, and it is difficult to downsize the gas sensor.

In contrast, according to the gas sensor of the present invention, the control unit corrects the output value of the detection element based on the resistance value of the heater. This allows the temperature compensation element to be omitted, and the downsizing of the gas sensor to be easily achieved.

In other words, the control unit estimates a temperature of the detection chamber based on a resistance value of the heater, and estimates a change in the resistance value of the detection element derived from a change in the temperature of the detection chamber (or change in environmental temperature). Then, the concentration of the gas to be detected may be detected by correcting the output value of the detection element such that the control unit, for example, offsets or reduces the change in the resistance value of the detection element derived from the change in the temperature of the detection chamber.

Further, in the gas sensor, preferably the detection element is a catalytic combustion element and the control unit corrects an output value of the detection element based on energy that operates the heater.

In the above mentioned construction, the control unit corrects the output value of the detection element based on the energy that operates the heater. This allows the temperature compensation element to be omitted, thereby to easily downsize the gas sensor.

That is, the control unit estimates a resistance value of the heater based on components of energy (an electric current value, a voltage value, or electric power or the like) that operates the heater, then estimates a temperature of the detection chamber based on the resistance value of the heater, and thereby estimates change in the resistance value of the detection element derived from the change in temperature of the detection chamber (or change in environmental temperature). Then, the concentration of the gas to be detected may be detected by correcting the output value of the detection element such that the control unit, for example, offsets or reduces the change in the resistance value of the detection element derived from the change in the temperature of the detection chamber.

Further, in the gas sensor, preferably the detection element detects hydrogen in a cathode off-gas discharged from the cathode of the fuel cell, and preferably the control unit corrects an output value of the detection element based on the temperature of the cathode off-gas.

In the above mentioned construction, the resistance value of the detection element in a catalytic combustion type is changed corresponding to the temperature of the cathode off-gas. For example, the higher the temperature of the cathode off-gas becomes, the larger the resistance value of the detection element becomes.

Accordingly, since the control unit corrects the output value of the detection element based on the temperature of the cathode off-gas, the gas sensor becomes more accurate.

As mentioned hereinbefore, according to the present invention, a gas sensor which needs no temperature sensor may be provided, the temperature sensor detecting a temperature of the heater for preventing the dew condensation.

DETAILED DESCRIPTION OF THE PREFERRED EMBODIMENT

First Embodiment

Figure 1:
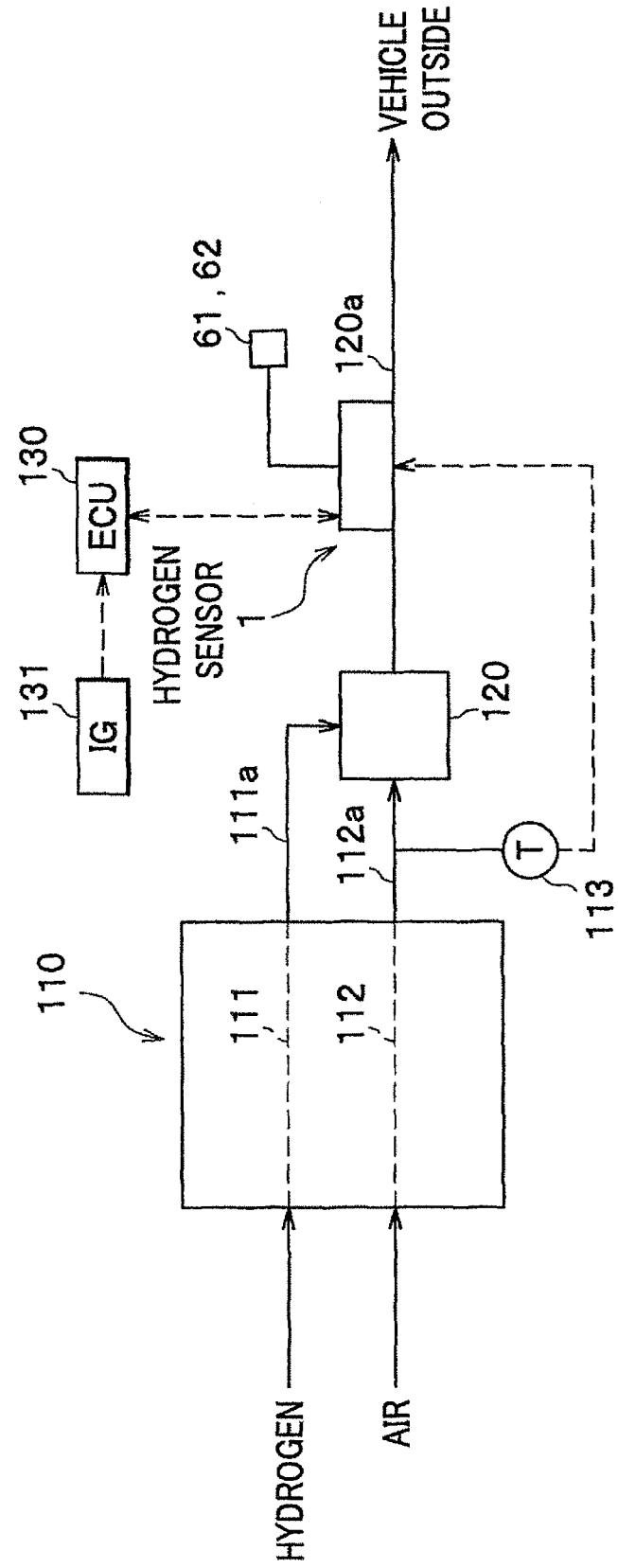
FIG. 1 is a diagram showing a schematic construction of the fuel cell system in the first embodiment.

Hereinafter, will be explained the first embodiment of the present invention referring to FIGS. 1 to 9.

First, a fuel cell system 100 incorporating a hydrogen sensor 1 (or gas sensor) will be explained. The fuel cell system 100 is mounted on a fuel cell vehicle (or moving body), comprising a fuel cell stack 110 (or fuel cell), a diluter 120, a temperature sensor 113, a hydrogen sensor 1, and ECU 130 (or Electric Control Unit).

<Fuel Cell Stack>

The fuel cell stack 110 is a polymer electrolyte fuel cell (or PEFC) and constructed by stacking a plurality of unit cells; the unit cell being made by sandwiching a membrane electrode assembly (or MEA) between separators (not shown). The MEA comprises an electrolytic membrane (or polymer electrolyte membrane), an anode and a cathode; the anode and the cathode sandwiching the MEA therebetween. An anode flow passage 111 and a cathode flow passage 112, comprised of grooves or through holes, are formed in each separator.

Further, when hydrogen is supplied from a hydrogen tank (not shown) to the anode through the anode flow passage 111, and air containing oxygen is supplied from a compressor (not shown) which takes in open air to the cathode through the cathode flow passage 112, an electrode reaction occurs on a catalyst (that is, Pt or the like) contained in the anode and the cathode, allowing the fuel cell stack 110 to generate electric power. When such a fuel cell stack 110 in a condition capable of generating electric power is electrically connected to an outside load (for example, a motor for traveling) thereby to output an electric current, the fuel cell stack 110 starts to generate electric power.

Moreover, an anode-off gas containing unconsumed hydrogen discharged from the anode flow passage 111 flows through a pipe 111a toward the diluter 120. In contrast, a cathode off-gas (or gas for dilution) discharged from the cathode flow passage 112 flows through a pipe 112a toward the diluter 120.

<Temperature Sensor>

The temperature sensor 113 is attached to the pipe 112a and detects a temperature of the cathode off-gas discharged from the cathode flow passage 112 and flowing toward the hydrogen sensor 1. Hereby, the temperature sensor 113 outputs the temperature data to a correction circuit 53 (see FIG. 4) of the hydrogen sensor 1 as explained hereinafter.

<Diluter>

The diluter 120 is a vessel for diluting hydrogen contained in the anode off-gas with the cathode off-gas or the like, and comprises a space for dilution inside the vessel. Then, the diluted gas containing hydrogen is discharged flowing through the pipe 120a to the outside of a vehicle.

<ECU>

The ECU 130 is constructed comprising a CPU, a ROM, a RAM, various types of interfaces, and an electronic circuit. Further, when the ECU 130 detects a turn-on signal of an IG 131, the ECU 130 outputs a start-up order to a microcomputer 51, a correction circuit 53 and a standard voltage generation circuit 54 of the hydrogen sensor 1 as described hereinafter (see FIG. 4). Note the IG 131 is a start-up switch of the fuel cell system 100 (or fuel cell vehicle) and arranged around a driver's seat.

<Construction of Hydrogen Sensor>

Figure 2:
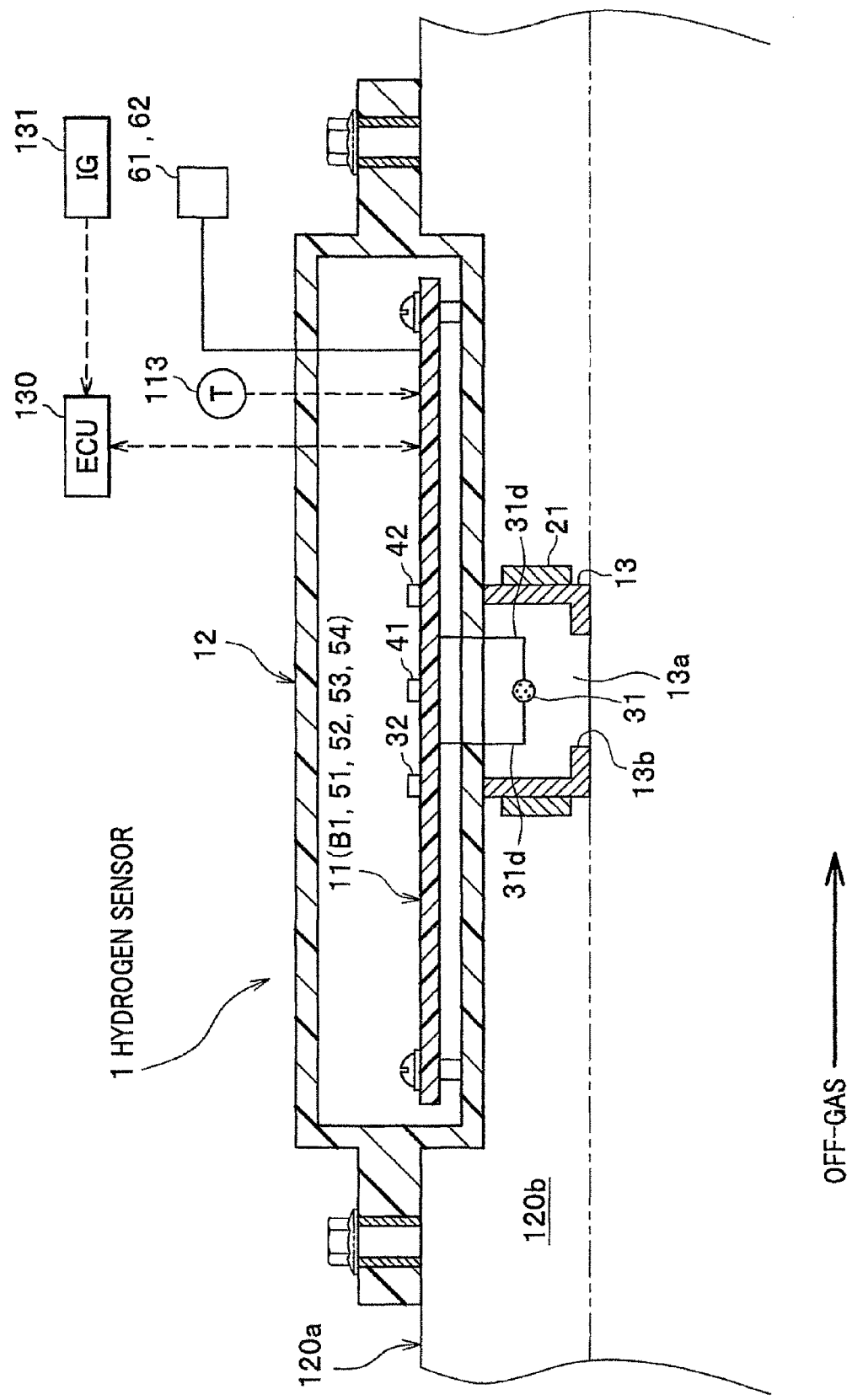
FIG. 2 is a diagram showing a side cross-section of the hydrogen sensor in the first embodiment.

As shown in FIG. 2, the hydrogen sensor 1 is a catalytic combustion sensor for detecting a hydrogen concentration contained in the gas flow through the pipe 120a by burning hydrogen using the detection sensor 31.

The hydrogen sensor comprises: a substrate 11 on which a predetermined circuit is formed, a case 12 in a thin box shape for housing the substrate 11, an element housing 13 in a cylindrical shape having a bottom part and extending vertically in a downward direction from a bottom wall part of the case 12, and a heater 21 in a cylindrical shape surrounding on the outside surface of the element housing 13.

However, the shape, the position and the number of the heater are not limited to the above mentioned construction. For example, the detection chamber 13a in the element housing 13 may be equipped with a plurality of plate shaped heaters.

The case 12 is made of a resin such as polyphenylene sulfide. The case 12 is attached to a ceiling wall part 120b of the pipe 120a by using bolts.

<Element Housing>

The element housing 13 comprises a detection chamber 13a therein for taking in gas that contains hydrogen, in order to detect hydrogen. In the detection chamber 13a, the detection element 31 is arranged as described hereinafter. That is, the element housing 13 houses the detection element 31.

The above mentioned element housing 13 is formed of a material with high a thermal conductivity (that is, metal such as SUS or the like, and resin with high thermal conductivity) such that the heater 21 transmits heat to the detection chamber 13a. Further, preferably the element housing 13 is constructed in a structure of fewer joints, for example, formed of an integrally molded part produced by extrusion molding, thereby to make the thermal resistance of the element housing 13 smaller. Moreover, the hydrogen sensor 1 is constructed to make the thermal conduction of the bottom part of the case 12 on which the element housing 13 is fixed lower thereby to make the thermal resistance of the bottom part of the case 12 larger. This construction allows a difference in the temperature between the heater 21 and the detection chamber 13a (or periphery of the detection element) to become small, when the temperature rises by the heater 21, for example, at the start-up time of the hydrogen sensor 1. This enables an error of the output by the hydrogen sensor 1 to become small.

Further, a gas inlet and outlet 13b in a circle shape looked from a plan view is formed at the bottom part of the element housing 13. Hereby, through the gas inlet and outlet 13b, the gas containing hydrogen goes in and out between the detection chamber 13a and the pipe 120a.

Note an explosion-proof filter and a water repelling filter (both not shown) are arranged such that the filters cover the gas inlet and outlet 13b. The explosion-proof filter secures an explosion proof performance and, for example, is formed of a metallic mesh or a porous material. The water repelling filter allows gas (or hydrogen) to pass through the filter, while the water repelling filter does not allow a liquid (or drop of water) to pass the filter. For example, the water repelling filter is made of a polytetrafluoroethylene membrane.

<Heater>

The heater 21 is an electric heater of a resistor, that is, a heat generator that generates heat by passing an electric current therethrough. The heater 21 has a large temperature resistance coefficient, and is formed of a material of which resistance value and temperature have a more or less linear relationship (see FIG. 3). The temperature resistance coefficient is also called a temperature coefficient of resistance, which represents a rate of a change in a resistance value to a change in a heater temperature. Herein, the unit of the temperature resistance coefficient is represented by "ppm/° C." in many cases.

A material having the above mentioned profile includes at least one kind of a metal such as platinum (Pt), molybdenum (Mo), tantalum (Ta), cupper (Cu), and a member selected from alloys such as nichrome and SUS. The heater temperature is estimated (or calculated) based on a resistance value of the heater 21 and a map shown in FIG. 3. Note a resistance value of the heater 21 is calculated based on, for example, an electric current value of the electric current passing the heater 21 and a voltage value of the voltage applied to the heater 21.

<Electric Current and Voltage Detector>

Figure 4:
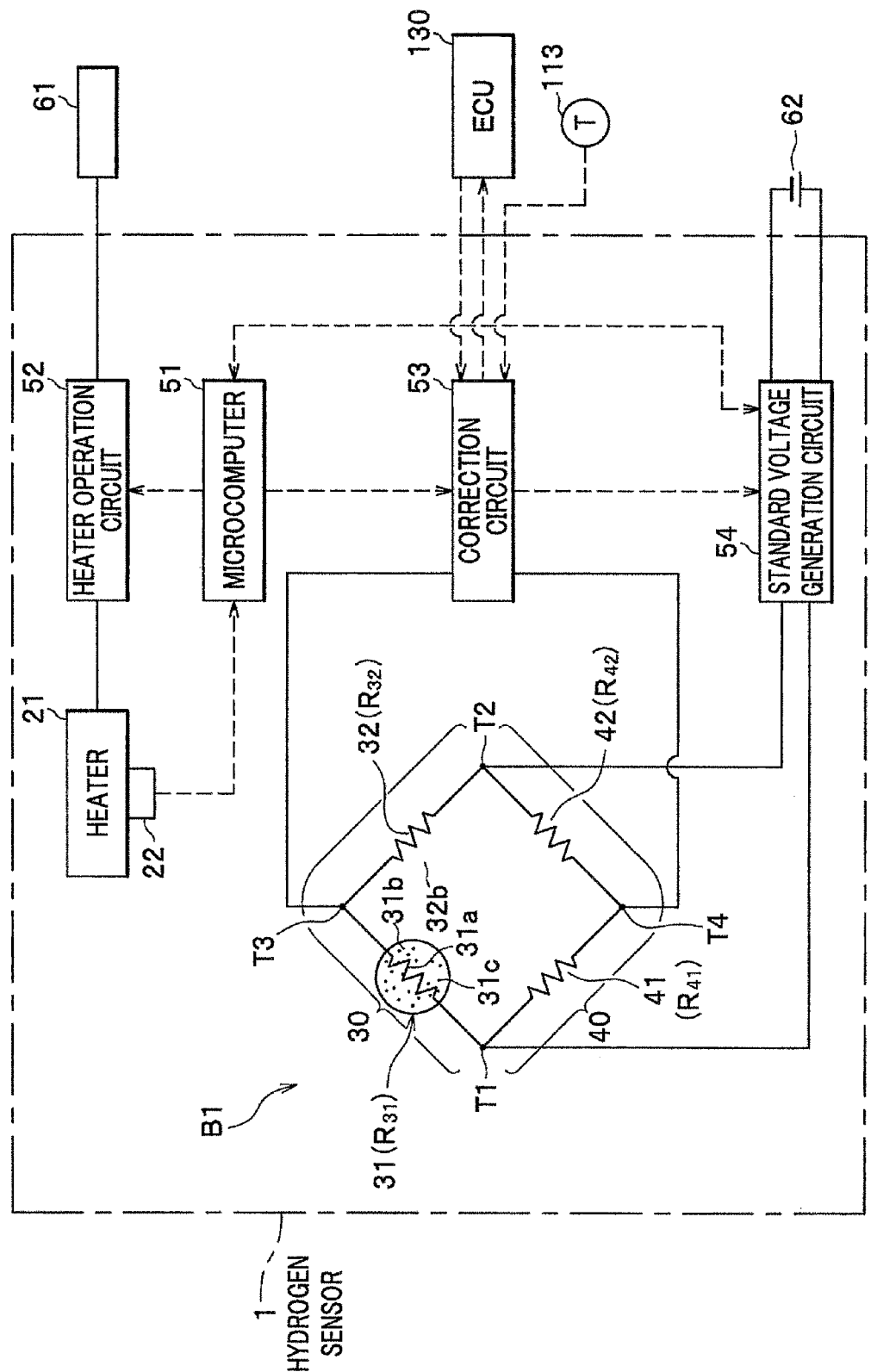
FIG. 4 is a circuit diagram showing the hydrogen sensor in the first embodiment.

The hydrogen sensor 1 comprises an electric current and voltage detector 22 as shown in FIG. 4. The electric current and voltage detector 22 is a device for detecting an electric current value of the electric current passing the heater 21, and a voltage value of the voltage applied to the heater 21, further including an electric current sensor and a voltage sensor. Then, the electric current and voltage detector 22 outputs the detected electric current value and voltage value to a microcomputer 51 as described hereinafter.

<Bridge Circuit>

The hydrogen sensor 1 comprises a bridge circuit B1 for detecting a concentration of hydrogen as shown in FIG. 4. The bridge circuit B1 comprises a first series side 30 and a second series side 40.

<Bridge Circuit—First Series Circuit>

The first series side 30 comprises a detection element 31 (or resistance value $R_{31}$) and a first resistor 32 (or resistance value $R_{32}$), the detection element 31 being connected with the first resistor 32 in series.

The detection element 31 is fixed to metallic stays 31d which virtually extend from the substrate 11 in a downward direction and compose a part of the first series circuit 30, and arranged in the detection chamber 13a (see FIG. 2).

In contrast, the first resistor 32 is attached on the substrate 11, and the resistance value $R_{32}$ thereof is a fixed value.

The detection element 31 is a known device that is active to hydrogen, and also called a catalyst resistor, comprising a coil 31a and a support 31b covering the coil 31a, an oxidation catalyst 31c being supported on the support 31b.

The coil 31a is made of a material with a large temperature resistance coefficient such as platinum (Pt) similarly to the heater 21. The support 31 is a porous material made of alumina or the like. The oxidation catalyst 31c is made of a precious metal (platinum or the like) that is highly active to hydrogen thereby to oxidize (or burn) hydrogen.

Therefore, the resistance value $R_{31}$ of the detection element 31 changes according to (1) the temperature of the detection chamber 13a (or environmental temperature, atmosphere temperature) and (2) the combustion heat generated by hydrogen contacting with the oxidation catalyst 31c thereby to burn (or oxidize).

<Bridge Circuit—Second Series Circuit>

The second series circuit 40 consists of a second resistor 41 (or resistance value $R_{41}$) and a third resistor 42 (or resistance value $R_{42}$), and is constructed by connecting the second resistor 41 with the third resistor 42 in series. The second resistor 41 and the third resistor 42 are mounted on the substrate 11. The resistance value $R_{41}$ of the second resistor 41 and the resistance value $R_{42}$ of the third resistor 42 are fixed values.

<Connecting State of First Series Circuit and Second Series Circuit>

Both ends of the first series circuit 30 and both ends of the second series circuit 40 are respectively connected to form input terminals T1 and T2. The input terminals T1 and T2 are connected with a standard voltage generation circuit 54. A voltage $V_{IN}$ generated by the standard voltage generation circuit 54 is applied to the input terminals T1 and T2 so as to pass the electric current through the bridge circuit B1.

In the first series circuit 30, an output terminal T3 is constructed at an intermediate point between the detection element 31 and the first resistor 32. Further, in the second series circuit 40, an output terminal T4 is constructed at an intermediate point between the second resistor 41 and the third resistor 42. Moreover, the output terminals T3 and T4 are connected with a correction circuit 53 so as to output a voltage $V_{OUT}$ (or output) of the bridge circuit B1 to the correction circuit 53.

Namely, the resistance value $R_{32}$ of the first resistor 32, the resistance value $R_{41}$ of the second resistor 41, and the resistance value $R_{42}$ of the third resistor 42 are fixed values. In contrast, the resistance value $R_{31}$ of the detection element 31 is changed based on (1) the temperature of the detection chamber 13a and (2) the combustion heat of hydrogen, whereby a potential difference ($V_{OUT}$) between the output terminals T3 and T4 is outputted to the correction circuit 53 as the output of the bridge circuit B1.

Thus, the output ($V_{OUT}$) of the bridge circuit B1 that changes according to the temperature of the detection chamber 13a and the combustion heat of hydrogen is inputted to the correction circuit 53. Herein, as mentioned hereinafter, the correction circuit 53 multiplies the correction coefficient α, which becomes smaller as the temperature of the detection chamber 13a becomes higher, with the output ($V_{OUT}$) of the bridge circuit B1. This process offsets or reduces a part of the output of the bridge circuit B1 obtained based on (1) the temperature change in the detection chamber 13a, whereby the resulting output of the bridge circuit B1 is corrected (or converted) to an output of the bridge circuit B1 being dependent on based on only the combustion heat of hydrogen (or hydrogen concentration).

Note, for example, the resistance value $R_{31}$ of the detection element 31, the resistance value $R_{32}$ of the first resistor 32, the resistance value $R_{41}$ of the second resistor 41, and the resistance value $R_{42}$ of the third resistor 42 are determined such that the output of the bridge circuit is 0 when the temperature of the detection chamber 13a is an ambient temperature (or 25° C.) and the hydrogen concentration is 0. Further, when the temperature of the detection chamber 13a is an ambient temperature (or 25° C.), the correction coefficient α is 1. Herein, there is a relationship that the correction coefficient α becomes smaller as the temperature of the detection chamber 13a becomes higher (see FIG. 6).

<Microcomputer and Heater Operation Circuit>

The hydrogen sensor 1 comprises a microcomputer 51 (or arithmetic processing device, control unit) and a heater operation circuit 52 (or control unit).

The microcomputer 51 comprises a CPU, a ROM, a RAM, various types of interfaces, and an electronic circuit or the like. Following programs stored in the microcomputer 51, the microcomputer 51 performs various functions.

Further, the microcomputer 51 has a function for calculating a resistance value of the heater 21 based on the electric current value and the voltage value of the heater 21, the values being inputted from the electric current and voltage detector 22. Moreover, the microcomputer 51 has a function for estimating (or calculating) the present temperature of the heater 21 based on the resistance value of the heater 21 and the map of FIG. 3. Furthermore, the microcomputer 51 has a function for outputting the resistance value of the heater 21 to the correction circuit 53 as described hereinafter.

Further, the microcomputer 51 has a function for controlling the heater operation circuit 52 (that is, PWM control, ON/OFF control or the like) based on the present temperature of the heater 21 and a target temperature of the heater 21. The target temperature of the heater 21 is set higher than the dew condensation temperature at which the humidity in the off-gas does not condense in the detection chamber 13a.

The heater operation circuit 52 comprises a DC-DC converter or the like, and is connected with an external power source 61 (or 12V battery or the like). Further, the heater operation circuit 52 has a function for supplying electric power from the external power source 61 to the heater 21 as changing the electric current value according to the order of the microcomputer 51.

<Correction Circuit and Standard Voltage Generation Circuit>

The hydrogen sensor 1 comprises the correction circuit 53 (or control unit) and the standard voltage generation circuit 54. The correction circuit 53 and the standard voltage generation circuit 54 are comprised of various types of electronic parts.

Figure 5:
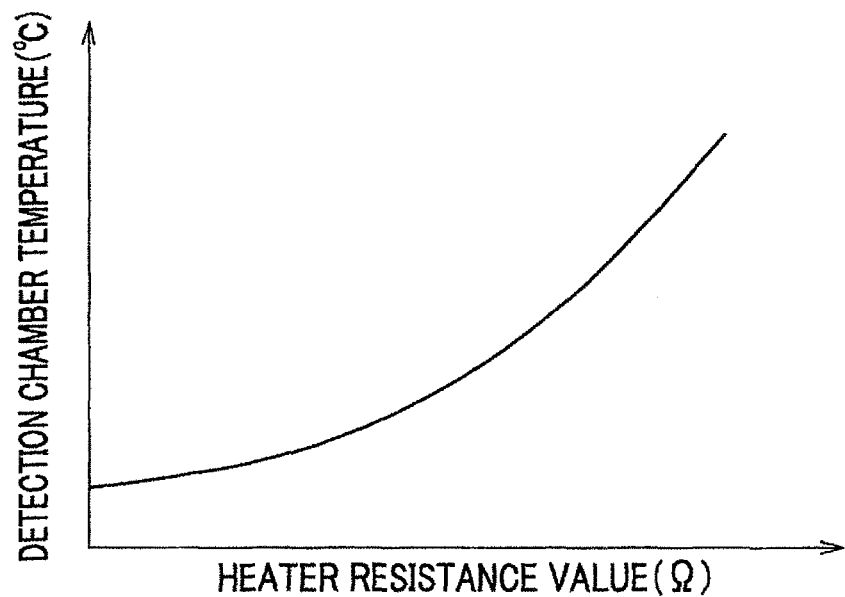
FIG. 5 is a map showing a relationship between a resistance value of the heater and a temperature of the detection chamber in the first embodiment.

The correction circuit 53 has a function for estimating (or calculating) a temperature of the detection chamber 13a based on the resistance value of the heater 21 inputted from the microcomputer 51 and the map in FIG. 5. The map in FIG. 5 is obtained in a pre-test or the like and stored in the correction circuit 53 in advance. As shown in FIG. 5, there is a relation ship that the larger the resistance of the heater 21 becomes, the higher the temperature of the detection chamber 13a becomes.

Figure 6:
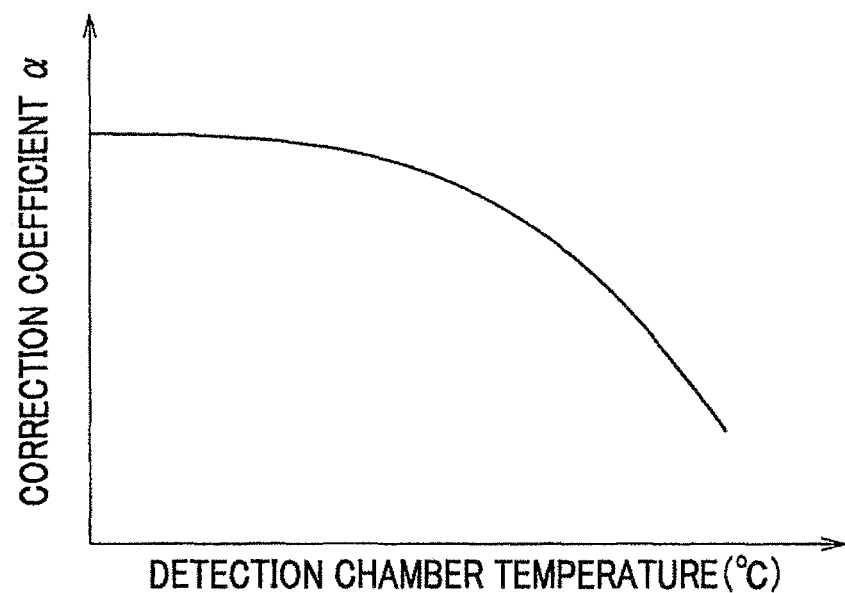
FIG. 6 is a map showing a relationship between a temperature of the detection chamber and a correction coefficient α for correcting the output of the bridge circuit in the hydrogen sensor of the first embodiment.

Further, the correction circuit 53 has a function for calculating the correction coefficient α for correcting the output of the bridge circuit B1 (or output of the hydrogen sensor 1) according to the temperature in the detection chamber 13a and the map in FIG. 6. The map in FIG. 6 is obtained in a pre-test or the like, and is stored in the correction circuit 53 in advance. As shown in FIG. 6, there is a relationship that the higher the temperature of the detection chamber 13a becomes, the smaller the correction coefficient α becomes.

Figure 7:
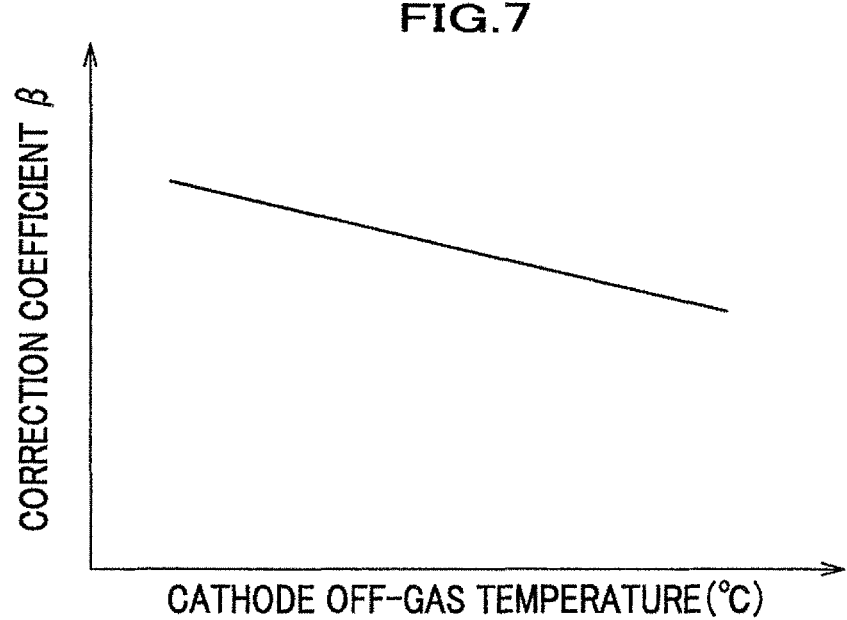
FIG. 7 is a map showing a relationship between a temperature of the cathode off-gas and a correction coefficient β for correcting the output of the bridge circuit in the hydrogen sensor of the first embodiment.

Further, the correction circuit 53 has a function for calculating the correction coefficient β for correcting the output of the bridge circuit B1 (or output of the hydrogen sensor 1) based on the temperature of the cathode off-gas detected through a temperature sensor 113 (see FIG. 1) and the map in FIG. 7. The map in FIG. 7 is obtained in a pre-test or the like in advance and stored beforehand in the correction circuit 53. As shown in FIG. 7, there is a relationship that the higher the temperature of the cathode off-gas becomes, the smaller the correction coefficient β becomes.

Then, the correction circuit 53 has a function for outputting the corrected output of the bridge circuit B1 to an ECU 130 through multiplying the output of the bridge circuit B1 ($V_{OUT}$) with the correction coefficient α and the correction coefficient β, thereby to correct the output of the bridge circuit B1.

The standard voltage generation circuit 54 comprises a DC-DC converter or the like and is connected to the external electric power source 62 (for example, 12V battery). Further, the standard voltage generation circuit 54 has a predetermined voltage applied to the bridge circuit B1.

<Operation of Hydrogen Sensor>

Next, operation of the hydrogen sensor will be explained referring to FIGS. 8 and 9.

<Heater Control Processing>

Figure 8:
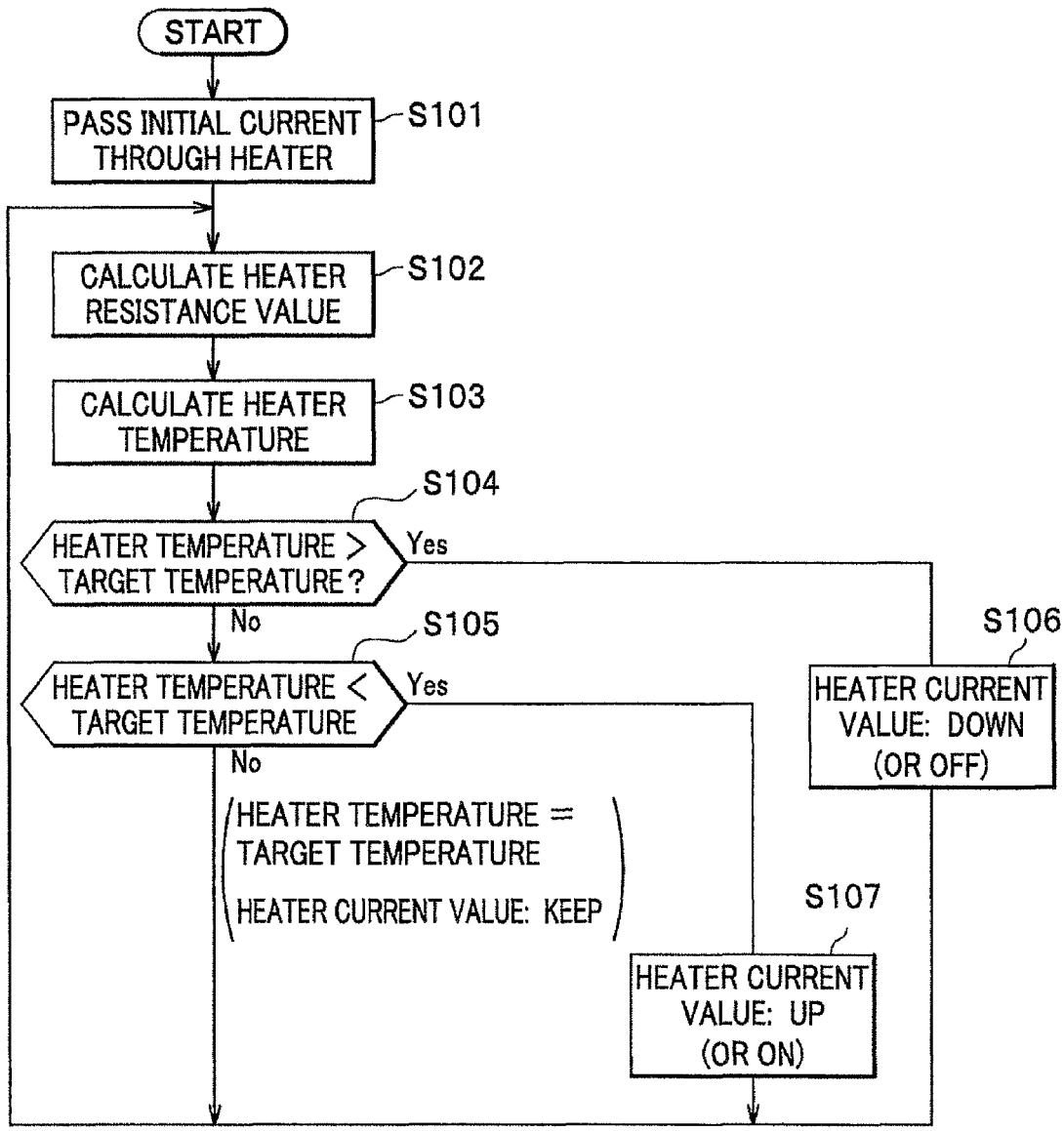
FIG. 8 is a flow chart showing a heater control process in the hydrogen sensor of the first embodiment.
Figure 9:
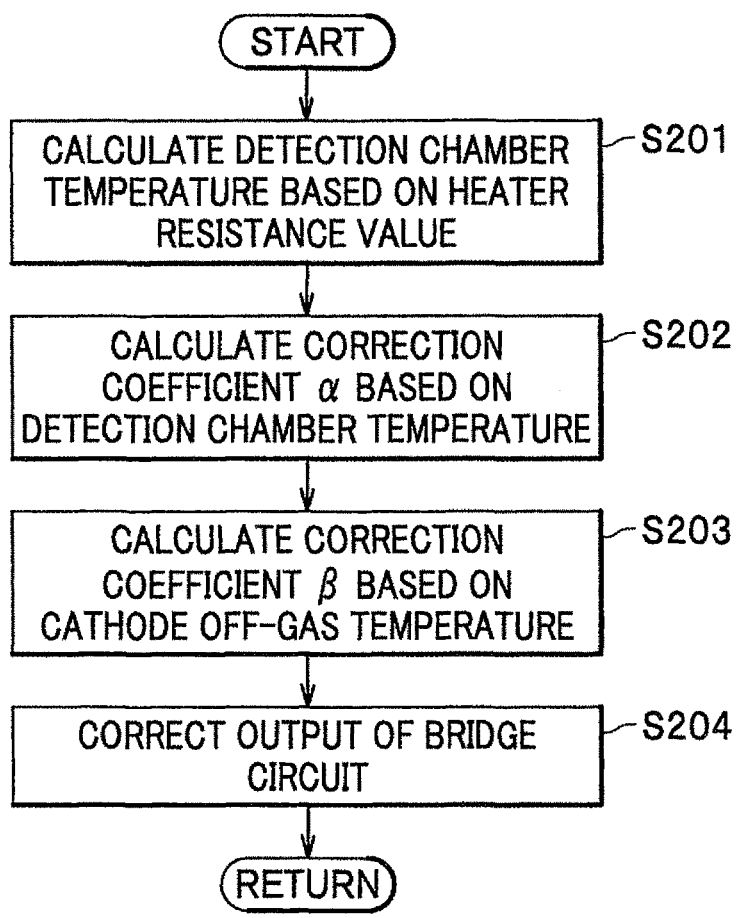
FIG. 9 is a flow chart showing an output correction process of the bridge circuit in the first embodiment.

Referring to FIG. 8, control processing of the heater 21 will be explained. Note when the IG 131 (or start-up switch) of the fuel cell system 100 (or fuel cell vehicle) is turned on, a series of steps in FIG. 8 are started. Further, in conjunction with the turning on of the IG 131, the standard voltage generation circuit 54 applies a standard voltage to the bridge circuit B1.

In the step S101, the microcomputer 51 outputs an order of passing an initial current through the heater to the heater operation circuit 52. Hereby, the heater operation circuit 52 supplies electric power from the outside power source 61 to the heater 21 by converting the electric current of the electric power to an initial electric current, and starts the passage of the electric current through the heater 21.

In the step S102, the microcomputer 51 calculates a resistance value of the heater 21 based on the electric current value and the voltage value of the heater 21, detected through the electric current and voltage detector 22.

Figure 3:
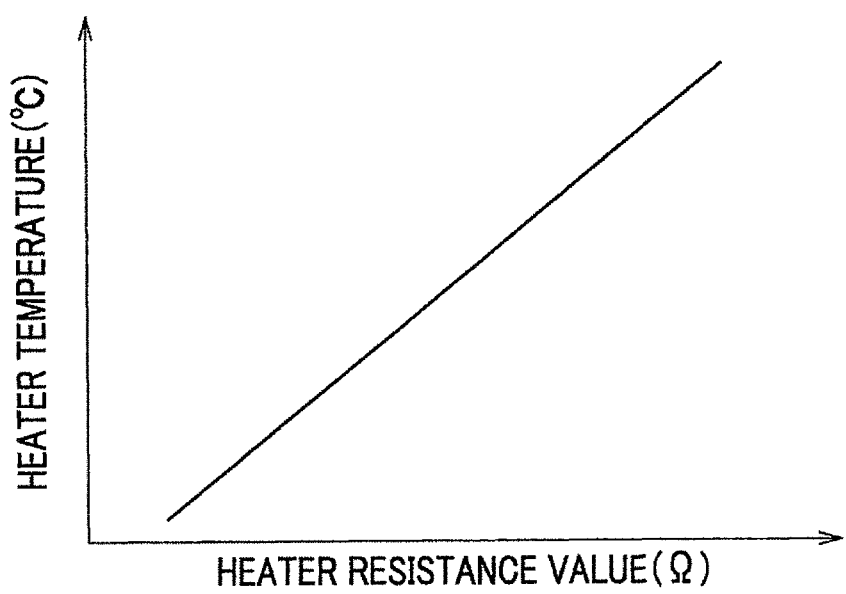
FIG. 3 is a map showing a relationship between a resistance value of the heater and a temperature of the heater in the first embodiment.

In the step S103, the microcomputer 51 calculates a temperature of the heater 21 based on the resistance value of the heater 21 calculated in the step S102 and the map in FIG. 3.

In the step S104, the microcomputer 51 judges whether or not the heater temperature calculated in the step S103 is higher than the target temperature.

If the microcomputer 51 judges that the heater temperature is higher than the target temperature (that is, S104=Yes), the processing of the microcomputer 51 goes to the step S106. On the other hand, if the microcomputer 51 judges that the heater temperature is not higher than the target temperature (that is, S104=No), the processing of the microcomputer 51 goes to the step S105.

In the step S105, the microcomputer 51 judges whether or not the heater temperature calculated in the step S103 is lower than the target temperature.

If the microcomputer 51 judges that the heater temperature is lower than the target temperature (that is, S105=Yes), the processing of the microcomputer 51 goes to the step S107. On the other hand, if the microcomputer 51 judges that the heater temperature is not lower than the target temperature (that is, S105=No), the processing of the microcomputer 51 goes to the step S102. Note if the processing of the microcomputer 51 goes to the step S102, the heater temperature is equal to the target temperature, and the electric current value passing through the heater 21 is to be maintained.

In the step S106, the microcomputer 51 outputs an order of decreasing a heater current value within the predetermined range to the heater operation circuit 52. Note the microcomputer 51 may output an order of having the heater current value become 0, namely, turning off the electric current through the heater 21. Further, the predetermined range is appropriately set by conducing pre-tests or the like.

Then, the heater operation circuit 52 decreases the electric current value through the heater 21 following the order of the microcomputer 51. Accordingly, the heating value of the heater 21 decreases, and the temperature of the heater 21 also starts to decrease. The above mentioned control processing allows the temperature of the heater 21 to be prevented from increasing too higher than the target temperature, thereby to be controlled at the target temperature.

After that, the processing of the microcomputer 51 goes to the step S102.

In the step S107, the microcomputer 51 outputs an order of increasing a heater current value within the predetermined range to the heater operation circuit 52. Note if the heater current value is 0, the microcomputer 51 may output an order of passing the initial electric current through the heater 21 to the heater operation circuit 52, and restart the passage of the electric current through the heater 21.

Then, the heater operation circuit 52 increases the electric current value through the heater 21 following the order of the microcomputer 51. Accordingly, the heating value of the heater 21 increases, and the temperature of the heater also starts to increase. The above mentioned control processing allows the temperature of the heater 21 to be prevented from decreasing too lower than the target temperature, thereby to be controlled at the target temperature.

After that, the processing of the microcomputer 51 goes to the step S102.

<Output Correction Processing>

Next, referring to FIG. 9, output correction processing of the bridge circuit B1 will be explained.

In the step S201, the correction circuit 53 calculates (or estimates) a temperature of the detection chamber 13a based on the resistance value of the heater 21, inputted from the microcomputer 51, and the map in FIG. 5.

In the step S202, the correction circuit 53 calculates a correction coefficient α based on the temperature of the detection chamber 13a, calculated in the step S201, and the map in FIG. 6.

In the step S203, the correction circuit 53 calculates a correction coefficient β based on the temperature of the cathode off-gas, detected through the temperature sensor 113, and the map in FIG. 7.

In the step S204, the correction circuit 53 multiplies the output of the bridge circuit B1 (or detection element) by the correction coefficient α calculated in the step S202 and the correction coefficient β calculated in the step S203 so as to correct the output of the bridge circuit B1, and, and outputs the corrected value as the output of the hydrogen sensor 1 to the outside (or ECU or the like of a fuel cell vehicle).

After tat, the processing of the correction circuit 53 goes back to "START" through "RETURN".

Effects of Hydrogen Sensor

According to the hydrogen sensor 1 described hereinbefore, the following effects will be achieved.

The heater 21 is formed of a material with a large temperature resistance coefficient and there is a relationship between the resistance value and the temperature thereof (see FIG. 3). This relationship allows the temperature of the heater 21 to be calculated based on the resistance value of the heater 21. Accordingly, a temperature sensor for only detecting the temperature of the heater 21 may be omitted, thereby to decrease the number of parts, resulting in the low cost production of the hydrogen sensor 1.

The target temperature of the heater 21 is set at the dew condensation temperature or more at which the steam in the off-gas does not condense, which prevents dew condensation water from adhering to the detection element 31.

A temperature of the detection chamber 13a and a correction coefficient α are calculated based on the resistance value of the heater 21, and the output of the bridge circuit B1 is corrected based on the correction coefficient α. That is, the output of the bridge circuit B1 is reduced based on the temperature of the detection chamber 13a, enabling a temperature compensation element to be omitted, which is inactive to hydrogen and of which resistance value is changed corresponding to the temperature of the detection chamber 13a. This allows downsizing of the element housing 13 to be achieved.

Further, a correction coefficient β is calculated based on the temperature of the cathode off-gas, and the output of the bridge circuit B1 is corrected based on the correction coefficient β. This enables the detected hydrogen concentration to be more accurate.

Modified Example

Hereinbefore, an embodiment of the present invention has been explained. However, the present invention is not limited to the embodiment. Therefore, the embodiment may be appropriately combined with a construction in another embodiment described hereinafter, or may be modified as mentioned below.

In the aforementioned embodiment, the construction in which gas to be detected is hydrogen has been exemplified. However, other gases may be detected.

Further, in the aforementioned embodiment, the construction in which a hydrogen sensor 1 is a catalytic combustion type has been exemplified. However, other types, for example, a gas sensor in a semiconductor type may be utilized.

Moreover, in the aforementioned embodiment, the construction in which a fuel cell vehicle is equipped with a fuel cell system 100 has been exemplified. However, other moving bodies, for example, a motorcycle, a train, a ship may be equipped with a fuel cell system 100. Furthermore, the present invention may be applied to a stand alone type of a fuel cell system for home use, and a fuel cell system incorporated in a hot water system.

Second Embodiment

Next, will be explained the second embodiment referring to FIGS. 10 to 13. Note the different parts form the first embodiment will be only explained, by omitting the same parts.

Construction of Hydrogen Sensor

Figure 10:
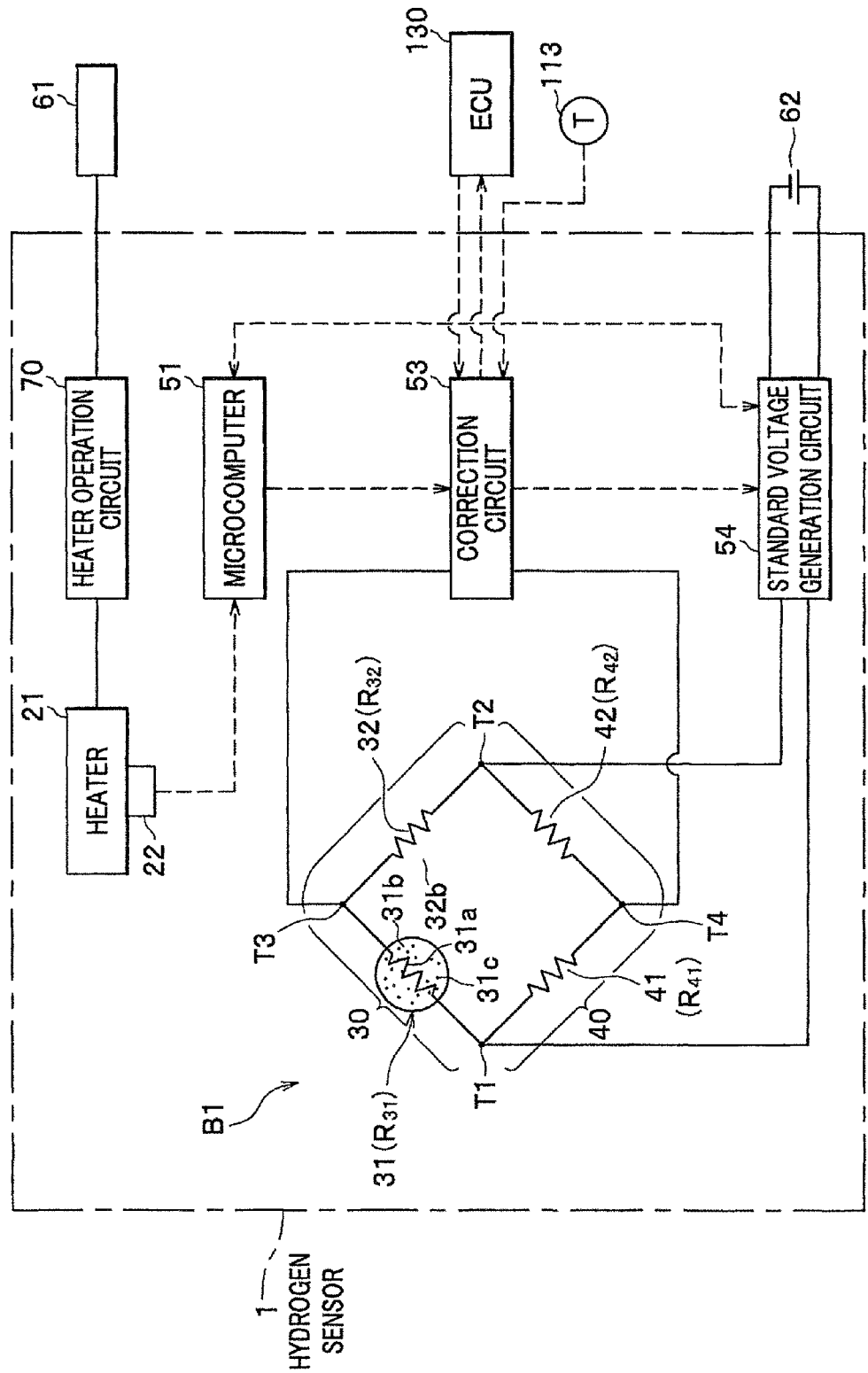
FIG. 10 is a circuit diagram showing the hydrogen sensor in the second embodiment.

As shown in FIG. 10, instead of the heater operation circuit 52 (see FIG. 4), a heater operation circuit 70 is included. Further, the microcomputer 51 does not control the heater operation circuit 70. Hereby, the control processing thereof is omitted.

<Heater Operation Circuit>

Figure 11:
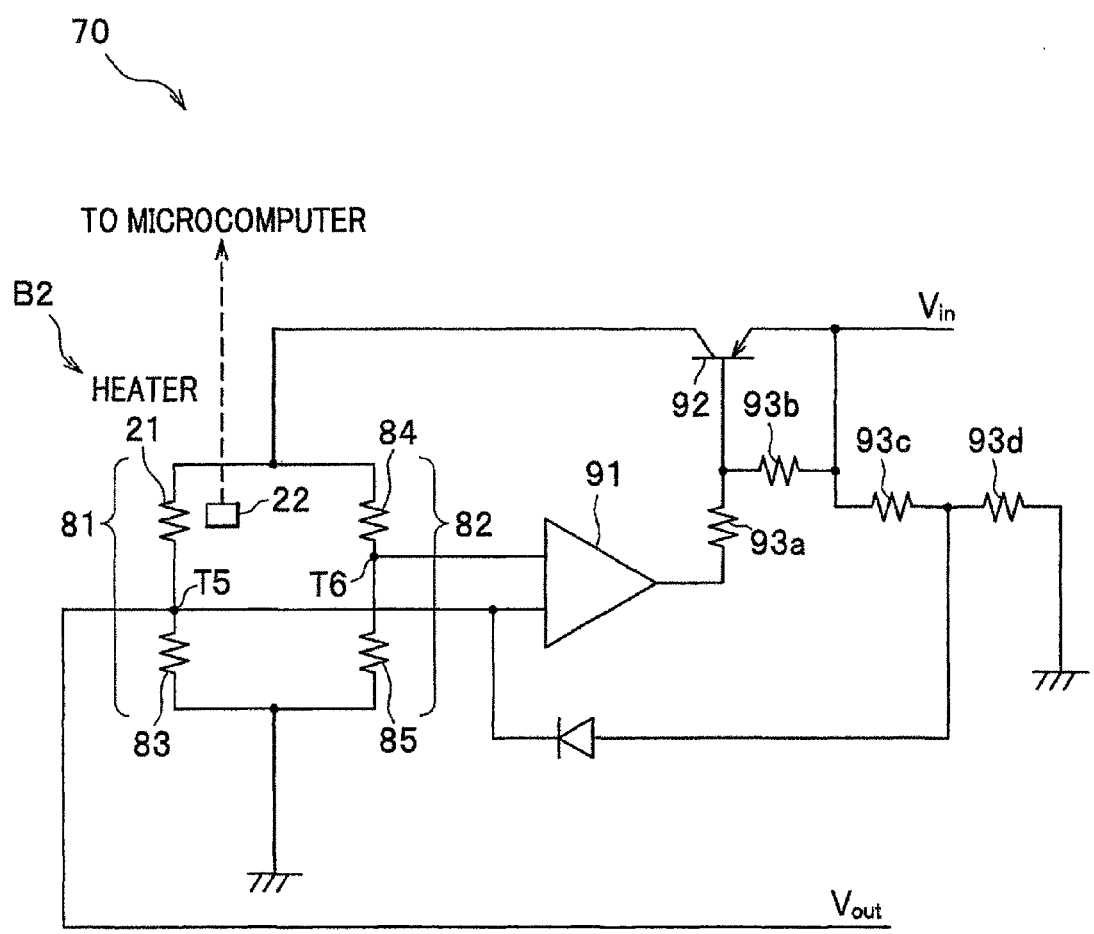
FIG. 11 is a circuit diagram showing the heater operation circuit in the second embodiment.
Figure 12:
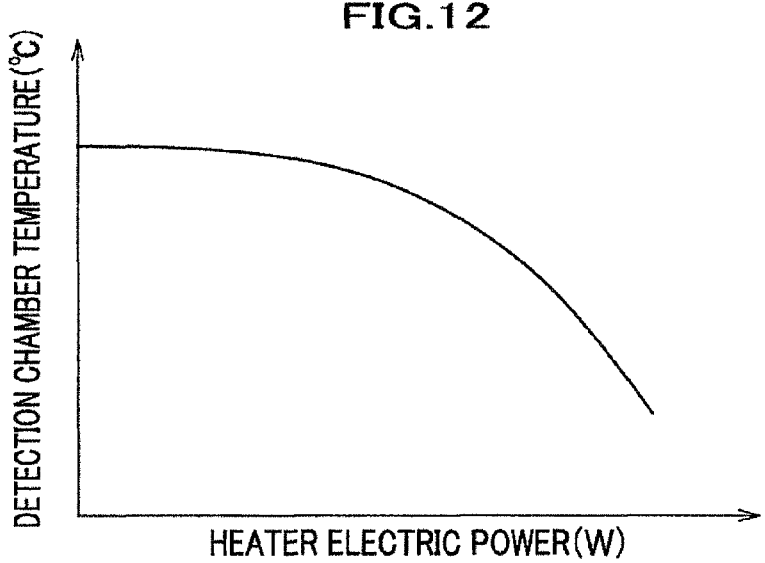
FIG. 12 is a map showing a relationship between electric power supplied to the heater and a temperature of the detection chamber in the second embodiment.

As shown in FIG. 11, a heater operation circuit 70 comprises a bridge circuit B2, an amplifier 91, and a transistor (IGBT or the like).

The bridge circuit B2 comprises a first branched part 81 and a second branched part 82, and is constructed by connecting the first branched part 81 and the second branched part 82 with the outside power source in parallel. The first branched part 81 is constructed by connecting the heater 21 and the A resistor 83 in series. The second branched part 82 is constructed by connecting the B resistor 84 and the C resistor 85 in series.

A rate between a resistance value $R_{84}$ of the B resistor 84 and a resistance value $R_{85}$ of the C resistor 85 is designed such that the rate is equal to a rate between a resistance value $R_{21}$ of the heater 21 and a resistance value $R_{83}$ of the A resistor 83.

Note preferably the sum of the resistance value $R_{84}$ of the B resistor 84 and the resistance value $R_{85}$ of the C resistor 85 is to be larger than the sum of the resistance value $R_{21}$ of the heater 21 at the target temperature and the resistance value $R_{83}$ of the A resistor 83. Hereby, this preferably makes the electric current hardly pass the second branched part 82.

Then, if the heater is not at a target temperature and does not have a target resistance value, a differential signal (or voltage difference) between a voltage of an output terminal T5 placed between the heater 21 and the A resistor 83 and a voltage of an output terminal T6 placed between the B resistor 84 and the C resistor 85 is inputted to the amplifier 91. Then, after the signal is amplified by the amplifier 91, the resulting signal is inputted into the transistor 92.

Then, when the signal is inputted as mentioned before, the transistor 92 becomes turned on, whereby an electric current supplied from the external power source passes the bridge circuit B2 including the heater 21.

In other words, the difference of the voltages between the output terminals T5 and T6 are fed back, thereby to change the amplified rate of the transistor 92. This process hereby changes the electric current passing the bridge circuit B2 until the rate between the resistance value $R_{21}$ of the heater 21 and the resistance value $R_{83}$ of the A resistor 83 (or voltage rate between the heater 21 and the A resistor 83) becomes equal to the rate between the resistance value $R_{84}$ of the B resistor 84 and the resistance value $R_{85}$ of the C resistor 85 (or voltage rate between the B resistor 84 and the C resistor 85). Accordingly, the above mentioned construction enables the temperature of the heater 21 to become equal to the target temperature.

Therefore, there is a relationship that the present resistance value and temperature of the heater 21 become smaller and lower as the electric current value and the voltage value of the heater 21 become larger, that is, as the electric power (or energy) supplied to the heater 21 becomes larger. Hereby, there is a relationship that the temperature of the detection chamber 13a becomes lower as the electric power supplied to the heater 21 becomes larger (see FIG. 12). Accordingly, it becomes possible to estimate (or calculate) the temperature of the detection chamber 13a based on the electric power supplied to the heater 21 and the map in FIG. 12.

Note in FIG. 11, the circuit comprised of resistors 93a, 93b, 93c and 93d is a circuit for supplying a base electric current which is used to operate the transistor 92.

Operation of Hydrogen Sensor

Next, operation of the hydrogen sensor 1 in the second embodiment will be explained.

Note, according to the second embodiment, the microcomputer 51 does not control a heater operation circuit 70, while the transistor 92 of the heater operation circuit 70 controls switching such that the temperature of the heater 21 becomes equal to the target temperature based on the output of the bridge circuit B2.

<Output Correction Processing>

Figure 13:
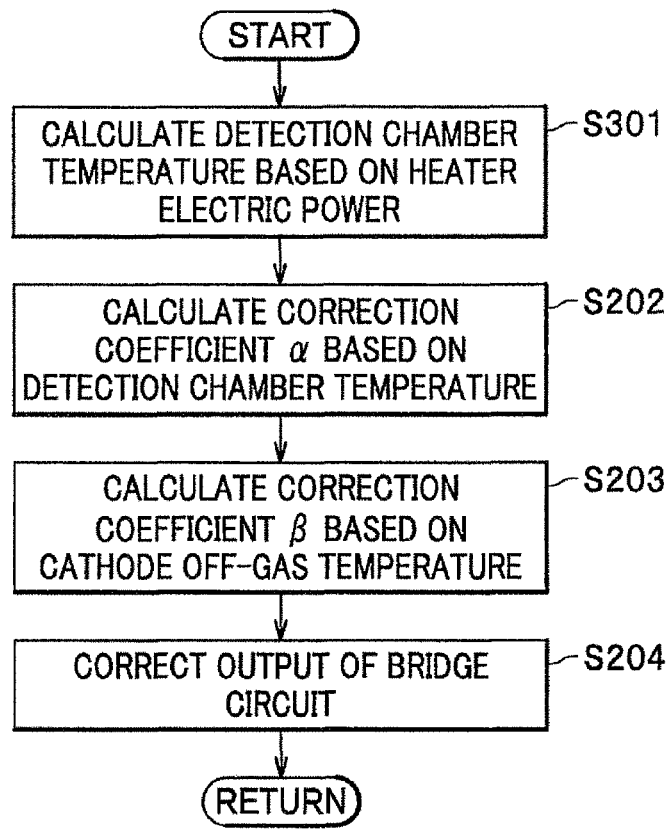
FIG. 13 is a flow chart showing an output correction process of the bridge circuit in the second embodiment.

Then, output correction processing by the hydrogen sensor 1 will be explained referring to FIG. 13. Herein, only the steps of the output correction processing different from the steps in FIG. 9 will be explained.

In the step S301, the microcomputer 51 calculates the electric power currently supplied (or distributed) to the hater 21, based on the electric current value and the voltage value of the heater detected through the electric current and voltage detector 22. Then, the microcomputer 51 calculates (or estimates) the temperature of the detection chamber 13a, based on the calculated electric power and the map in FIG. 12.

Alternatively, another construction of the microcomputer 51 may be applicable, in which the electric power is not calculated and the temperature of the detection chamber 13b is calculated (or estimated) based on the electric current value and the voltage value.

After that, the processing of the microcomputer 51 goes to the step S202.

Effect of Hydrogen Sensor

The above mentioned hydrogen sensor may provide the following effects.

That is, the heater operation circuit 70 in itself is constructed to control the heater temperature so as to become equal to the target temperature. This construction enables the microcomputer 51 to omit the control processing of the heater 21.

Further, the resistance value of the heater 21 is calculated based on the electric power supplied to the heater 21. The temperature of the detection chamber 13a and the correction coefficient α are calculated based on the calculated resistance value of the heater 21. Moreover, the output of the bridge circuit B2 is corrected based on the calculated correction coefficient α. The above mentioned processes enable the temperature compensation element to be omitted, which is inactive to hydrogen and of which resistance value is changed corresponding to the temperature of the detection chamber 13a. Accordingly, the element housing 13 may be downsized.

What is claimed is:

1. A gas sensor comprising:
an element housing having a detection chamber into which gas to be detected is introduced;
a detection element arranged in the detection chamber and detecting the gas to be detected;
a heater for heating the detection chamber by generating heat through passing an electric current via the heater, whereby a resistance value of the heater is changed corresponding to a temperature of the detection chamber, wherein the heater is located on an outside surface of the element housing;
a case having a bottom wall part on which the element housing is fixed; and
a control unit for controlling the heater, wherein
the control unit controls the temperature of the detection chamber by adjusting the electric current passing through the heater, based on the resistance value of the heater, and
wherein the bottom wall part of the case has lower thermal conductivity and larger thermal resistance than the element housing.

2. The gas sensor as described in claim 1, further comprising
a bridge circuit which is constructed by including the heater, an A resistor, a B resistor and a C resistor, wherein
the control unit includes a heater operation circuit for feeding back a voltage difference outputted from the bridge circuit, thereby to control the electric current through the heater.

3. The gas sensor as described in claim 1, wherein the control unit controls the temperature of the detection chamber to be kept at a temperature of preventing dew condensation or more such that the dew condensation in the detection chamber is prevented.

4. The gas sensor as described in claim 1, wherein
the detection element is a catalytic combustion element and outputs an output value thereof corresponding to the gas to be detected; and
the control unit corrects the output value of the detection element based on the resistance value of the heater.

5. The gas sensor as described in claim 1, wherein
the detection element is a catalytic combustion element; and
the control unit corrects the output value of the detection element, based on energy that operates the heater.

6. The gas sensor as described in claim 4, wherein
the detection element detects hydrogen in cathode off-gas discharged from the cathode of a fuel cell; and
the control unit corrects the output value of the detection element, based on a temperature of the cathode off-gas.

* * * * *